United States Patent [19]

Pfenninger et al.

[11] Patent Number: 4,749,795

[45] Date of Patent: Jun. 7, 1988

[54] PHENYL SUBSTITUTED PYRROLINONES

[75] Inventors: Johannes Pfenninger, Marly; Abul Iqbal, Ettingen; Alain C. Rochat, Fribourg, all of Switzerland

[73] Assignee: Ciba-Geigy Corporation, Ardsley, N.Y.

[21] Appl. No.: 34,374

[22] Filed: Apr. 6, 1987

Related U.S. Application Data

[62] Division of Ser. No. 793,868, Nov. 1, 1985, Pat. No. 4,681,971.

[30] Foreign Application Priority Data

Nov. 7, 1984 [CH] Switzerland .................. 5358/84

[51] Int. Cl.⁴ ......................................... C07D 207/277
[52] U.S. Cl. ..................................................... 548/531
[58] Field of Search ........................................ 548/531

[56] References Cited

FOREIGN PATENT DOCUMENTS 0022551 1/1981 European Pat. Off. .

*Primary Examiner*—Joseph P. Brust
*Attorney, Agent, or Firm*—Luther A. R. Hall

[57] ABSTRACT

The invention relates to pyrrolinones of formula (1)

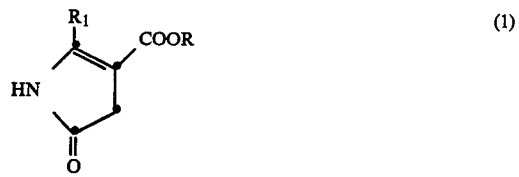

wherein $R_1$ is an alkyl group containing at least 2 carbon atoms, an aralkyl group, an isocyclic or heterocyclic aromatic radical and R is an alkyl or aryl group.

The invention also relates to aminodicarboxylates of formula (2)

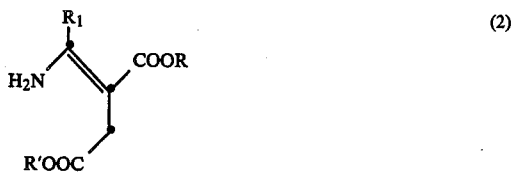

wherein $R_1$ is a defined in claim 1 and R and R' are the same or different and are alkyl or aryl.

The aminodicarboxylates of formula (2) are prepared by condensing a disuccinate of the formula $R'OOCCH_2CH_2COOR$ with a nitrile of the formula $R_1CN$, in the presence of a strong base and zinc chloride.

The pyrrolinones of formula (1) are obtained by reacting the aminodicarboxylates of formula (2) in the presence of a strong base in an organic solvent.

The compounds of formulae (1) and (2) are valuable intermediates for pigments.

3 Claims, No Drawings

PHENYL SUBSTITUTED PYRROLINONES

This is a divisional of application Ser. No. 793,868, filed on Nov. 1, 1985, now U.S. Pat. No. 4,681,971, issued on July 21, 1987.

The invention relates to novel pyrrolinones of formula (1)

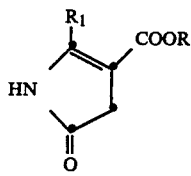

(1)

wherein $R_1$ is an alkyl group containing at least 2 carbon atoms, an aralkyl group, an isocyclic or heterocyclic aromatic radical and R is an alkyl or aryl group.

R in formula (1) as an alkyl group may be branched or unbranched of formula $C_nH_{2n+1}$ or cyclohexyl, and contains preferably 1 to 18, in particular 1 to 12 and most preferably 1 to 4, carbon atoms, e.g. methyl, ethyl, isopropyl, sec-butyl, tert-butyl, tert-amyl and cyclohexyl.

R as an aryl group may be in particular phenyl which is unsubstituted or substituted by nitro, halogen such as chlorine, $C_1$-$C_6$alkyl such as methyl, ethyl, isopropyl or tert-butyl, or $C_1$-$C_6$alkoxy such as methoxy or ethoxy. Aryl is preferably unsubstituted phenyl.

$R_1$ in formula (1) as an alkyl group may be branched or unbranched of formula $C_nH_{2n+1}$ or cyclohexyl, and contains preferably 2 to 18, in particular 4 to 18, more particularly 6 to 18 and most preferably 10 to 18, carbon atoms, e.g. ethyl, isopropyl, sec-butyl, tert-butyl, tert-amyl, cyclohexyl, octyl, decyl, dodecyl or stearyl.

$R_1$ as an aralkyl group is preferably one which contains a preferably mono- to tricyclic, most preferably mono- or bicyclic, aryl radical which is attached to a branched or unbranched alkyl or alkenyl group containing 1 to 12, preferably 1 to 6 and most preferably 1 to 4, carbon atoms. Examples of such aralkyl groups are benzyl and phenylethyl.

$R_1$ as an isocyclic aromatic radical is preferably a mono- to tetracyclic, most preferably mono- or bicyclic, radical, e.g. a phenyl, diphenylyl or naphthyl radical.

$R_1$ as a heterocyclic aromatic radical is preferably a mono- to tricyclic radical. Said radical may be purely heterocyclic or may be a heterocyclic ring and may contain one or more fused benzene rings, e.g. pyridyl, pyrimidyl, pyrazinyl, triazinyl, furanyl, pyrrolyl, thiophenyl, quinolyl, coumarinyl, benzofuranyl, benzimidazolyl or benzoxazolyl. Both the isocyclic and the heterocyclic aromatic radicals may contain the conventional substituents as cited for example in European published application 94 911.

$R_1$ is preferably a radical of the formula

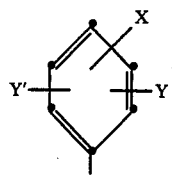

wherein each of X, Y and Y' independently is a hydrogen or halogen atom, a carbamoyl, trifluoromethyl, cyano, $C_2$-$C_6$alkylcarbamoyl, $C_1$-$C_6$alkyl, $C_1$-$C_6$alkoxy, $C_1$-$C_6$alkylmercapto, $C_2$-$C_6$alkoxycarbonyl, $C_2$-$C_6$alkanoylamino or $C_2$-$C_6$dialkylamino group; or is a phenoxy, phenylmercapto, phenoxycarbonyl, phenylcarbamoyl or benzoylamino group each unsubstituted or substituted by halogen, $C_1$-$C_6$alkyl or $C_1$-$C_6$alkoxy, at least one of the substituents X, Y and Y' being a hydrogen atom, and $R_1$ is most preferably a radical of the formula

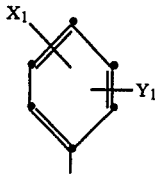

wherein one of the substituents $X_1$ and $Y_1$ is a hydrogen, chlorine or bromine atom, a methyl, cyano, N,N-dimethylamino, N,N,diethylamino, $C_1$-$C_6$alkoxy, $C_2$-$C_4$alkoxycarbonyl or $C_2$-$C_4$alkylcarbamoyl group, or a phenylcarbamoyl group which is unsubstituted or substituted by chlorine, methyl or methoxy, and the other substituent is a hydrogen atom. The substituents X, $X_1$, Y, Y' and $Y_1$ are in parameta- or ortho-position, preferably in meta- and para-position, to the pyrrolinone group.

The pyrrolinones of formula (1) are obtained for example by cyclising an aminodicarboxylate of formula (2)

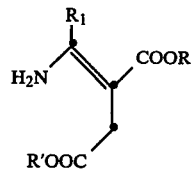

(2)

wherein $R_1$ and R are as defined above and R' has the meanings given for R and may be the same as or different from R, with a strong base.

The cyclisation is carried out in the presence of a strong base in an organic solvent.

Examples of suitable bases are: alkali metal hydroxides such as sodium, potassium or lithium hydroxide, or alkaline earth metal hydroxides such as calcium or magnesium hydroxide, or alkali metal amides such as lithium amide or lithium diisopropylamide, lithium diethylamide or lithium isopropylcyclohexylamide or sodium amide, or alkali metal hydrides such as lithium hydride or sodium hydride, or alkaline earth metal hydrides such as calcium hydride, or alkaline earth metal alcoholates or alkali metal alcoholates which are derived preferably from primary, secondary or tertiary aliphatic alcohols containing 1 to 10 carbon atoms, e.g. sodium, potassium or lithium methylate, sodium, potassium or lithium ethylate, sodium, potassium or lithium n-propylate, sodium potassium or lithium isopropylate, sodium, potassium or lithium n-butylate, sodium, potassium or lithium sec-butylate, sodium, potassium or lithium tert-butylate, sodium potassium or lithium 2-methyl-2-butylate, sodium, potassium or lithium 2-methyl-2-pentylate, sodium potassium or lithium 3-methyl-3-pentylate, sodium potassium or lithium 3-ethyl-3-pentylate, or alkaline earth metal phenolates, alkaline earth metal o-alkyl substituted phenolates, alkali metal phenolates or alkali metal o-alkyl substituted phenolates, e.g. sodium or potassium o-cresolate. However, a mixture of the above bases may also be employed.

Preferred strong bases are alkali metal alcoholates, the alkali metal preferably being sodium or potassium and the alcoholate being preferably derived from a primary or secondary alcohol. Particularly preferred strong bases are therefore e.g. sodium or potassium methylate, sodium or potassium ethylate, sodium or potassium isopropylate, sodium or potassium sec-butylate, sodidum or potassium tert-butylate and sodium or potassium tert-amylate. The alkali metal alcoholates may also be prepared in situ by reacting the appropriate alcohol with the alkali metal, alkali metal hydride or alkali metal amide.

The strong base is employed in an amount of preferably 0.1 to 10 moles, most preferably 0.9 to 4.0 moles, based on 1 mole of the reactant of formula (2).

Examples of suitable solvents are: primary, secondary or tertiary alcohols containing 1 to 10 carbon atoms, e.g. methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol, 2,4,4-trifluoromethyl-2-pentanol, or glycols such as ethylene glycol or diethylene glycol; and also ethers such as tetrahydrofuran or dioxane, or glycol ethers such as ethylene glycol methyl ether, ethylene glycol ethyl ether, diethylene glycol monomethyl ether or diethylene glycol monoethyl ether; as well as dipolar aprotic solvents such as acetonitrile, benzonitrile, dimethylformamide, N,N-dimethylacetamide, nitrobenzene or N-methyl-pyrrolidone; aliphatic or aromatic hydrocarbons such as benzene or benzene substituted by alkyl, alkoxy or halogen, e.g. toluene, xylene, anisole or chlorobenzene; or aromatic N-heterocyclic rings such as pyridine, picoline or quinoline. A mixture of the above solvents may also be employed.

The reactions are preferably carried out at a temperature in the range from 20° to 100° C., most preferably from 40° to 80° C.

If the solvent employed is an alcohol and the base an alcoholate, it may be advantageous to select an alcohol and an alcoholate containing the same alkyl moieties. It may also be of advantage if the ester of formula (2) also contains such alkyl groups.

The pyrrolinones of formula (1) are also obtained by known methods by cyclising a compound of formula (3)

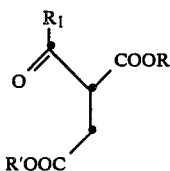
(3)

for example with ammonium salts.

The compounds of formula (3) are known and may be obtained e.g. by condensing an acylacetate ester of formula (4)

wherein $R_1$ and R are as defined above, with an ester of the formula $XCH_2COOR'$, wherein X is a fluorine, chlorine, bromine or iodine atom and R' is as defined above (q.v. W. H. Perkin, J. Chem. Soc. 47, p. 262 or Org. Synth. 42, 75 (1962)).

The aminodicarboxylates of formula (2) constitute a further object of the present invention. They are obtained for example by reacting a disuccinate of formula (5)

with a nitrile of the formula $R_1CN$, in which formulae R, R' and $R_1$ are as defined above, in the presence of a strong base and a zinc or magnesium compound, by processes analogous to those described in Chem. Lett. 1982, p. 687 and Tetrahedron Lett. 1982, p. 1957.

The disuccinates of formula (5) may be dialkyl, diaryl or monoalkylmonoaryl succinates. The dialkyl and diaryl succinates may also be unsymmetrical. However, it is preferred to use symmetrical disuccinates, most preferably symmetrical dialkyl succinates. If a diaryl or monoaryl-monoalkyl succinate is employed, aryl is preferably phenyl which is unsubstituted or substituted by halogen such as chlorine, $C_1$–$C_6$alkyl such as methyl, ethyl, isopropyl or tert-butyl, or $C_1$–$C_6$alkoxy such as methoxy or ethoxy. The preferred meaning of aryl is unsubstituted phenyl. If a dialkyl or monoalkyl-monoaryl succinate is employed, then alkyl may be unbranched or branched, preferably branched, and may contain preferably 1 to 18, in particular 1 to 12, more particularly 1 to 8 and most preferably 1 to 5, carbon atoms. Branched alkyl is preferably sec-alkyl or tert-alkyl, e.g. isopropyl, sec-butyl, tert-butyl or tert-amyl.

Examples of disuccinates of formula (5) are: dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, di-[1,1-dimethylbutyl]succinate, di-[1,1,3,3-tetramethylbutyl]succinate, di-[1,1-dimethylpentyl]succinate, di-[1-methyl-1-ethylbutyl]succinate, di-[1,1-diethylpropyl]succinate, diphenyl succinate, di-[4-methylpentyl]succinate, di-[2-methylphenyl]succinate, di-[4-chlorophenyl]succinate, monoethylmonophenyl succinate and dicyclohexyl succinate.

Examples of nitriles are: acetonitrile, propionitrile, butyronitrile, isobutyronitrile, hexyl cyanide, cyclohexyl cyanide, benzyl cyanide, benzonitrile, o-, m- or p-chlorobenzonitrile, p-bromobenzonitrile, o-, m- or p-methylbenzonitrile, p-tert-butylbenzonitrile, p-phenylbenzonitrile, p-methoxybenzonitrile, p-phenoxybenzonitrile, 3,4-dimethylbenzonitrile, isophthalonitrile, terephthalonitrile, 3-pyridyl cyanide or 4-pyridyl cyanide.

The strong bases listed as being suitable for the cyclisation of the aminodicarboxylates of formula (2) are also suitable for the above process.

Preferred strong bases are alkali metal amides, the alkali metal preferably being lithium and the amide being preferably derived from a secondary amine. Particularly preferred strong bases are therefore e.g. lithium diisopropylamide, lithium diethylamide or lithium isopropylcyclohexylamide. The alkali metal amides may also be prepared in situ by reacting the appropriate amine with an alkali metal alkyl compound, the alkali metal, alkali metal hydride or alkali metal amide.

The strong base is employed in an amount of preferably 0.1 to 10 moles, most preferably 0.9 to 4.0 moles, based on 1 mole of the reactant of formula (5).

The required zinc and magnesium compounds may be employed, inter alia, in the form of salts of inorganic acids (e.g. halides), salts of organic acids (e.g. acetates), or in the form of alcoholates.

The solvents indicated as being suitable for the cyclisation of the aminodicarboxylates of formula (2) are also suitable for this process.

Particularly preferred solvents are those which are inert towards strong bases, i.e. aromatic hydrocarbons such as benzene, benzenes substituted by alkyl, alkoxy or halogen, or ethers such as diethyl ether, tetrahydrofuran, dioxane, anisole, ethylene glycol dimethyl ether or diethylene glycol dimethyl ether, and heterocylcic aromatic hydrocarbons such as pyridine, picoline or quinoline.

The reactions are preferably carried out at a temperature in the range from 20° to −100° C., most preferably from −20° to −80° C.

The isolation of the compounds of formulae (1) and (2) is conveniently effected by hydrolysis of the reaction mixture, extraction with an organic solvent and removal of the latter.

The hydrolysis of the condensation product may be carried out with an acid, an alcohol containing 1 to 4 carbon atoms, e.g. methanol or ethanol, but preferably with water. Examples of suitable acids are: aliphatic or aromatic carboxylic or sulfonic acids, e.g. formic acid, acetic acid, propionic acid, oxalic acid, benzoic acid or benzenesulfonic acid. Further suitable acids are also mineral acids, e.g. hydrochloric acid, aqueous solutions thereof, as well as carbonic acid, dilute sulfuric acid and dilute phosphoric acid.

The compounds of formulae (1) and (2) are valuable intermediates which are suitable for example for the preparation of dyes and pigments, in particular for the preparation of pyrrolo[3,4-c]pyrrols.

The invention is illustrated by the following Examples.

EXAMPLE 1

In a reaction vessel which has been cooled to −78° C. by a mixture of dry ice and isopropanol, 13.8 ml of a 1.6 molar solution of n-butyl lithium in hexane and 3.1 ml of diisopropylamine are added under a nitrogen atmosphere to 70 ml of anhydrous tetrahydrofuran. After 20 minutes, 2.3 g of di-tert-butyl succinate in 5 ml of tetrahydrofuran are added and the mixture is stirred for 50 minutes. To the reaction mixture are then added 10 ml of a 1 molar solution of zinc chloride in tetrahydrofuran, followed after 30 minutes by the addition of 2.1 g of benzonitrile. After 2 hours, the reaction mixture is allowed to warm to room temperature and is then poured into 200 ml of water. The resultant mixture is taken up in ethyl acetate, the organic phase is washed with a concentrated solution of sodium chloride and dried over sodium sulfate and the solvent is removed by rotary evaporation. Chromatography over silica gel (elution with an 8:1 mixture of hexane and ethyl acetate) affords 1.96 g (59% of theory, based on the di-tert-butyl succinate) of the compound of formula (6)

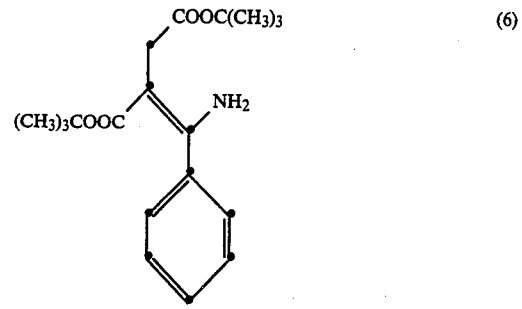

(or of the corresponding Z isomer) in the form of colourless crystals.

m.p.: 112°–114° C., UV (MeOH, $\lambda_{max}$, $\epsilon$): 222 (6750), 288 (13750).

$C_{19}H_{27}NO_4$ calc.: C 68.44; H 8.16; N 4.20; found: C 68.37; H 8.16; N 4.21.

EXAMPLE 2

The procedure of Example 1 is repeated, using 4-chlorobenzonitrile instead of benzonitrile. The product of formula (7)

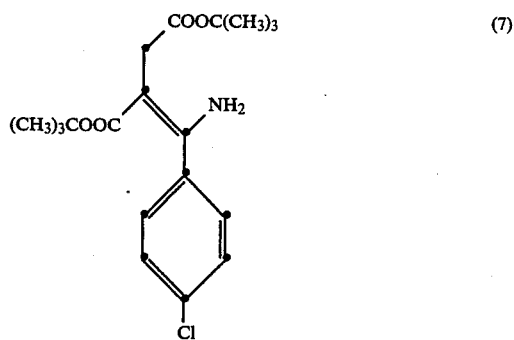

(or the corresponding Z isomer) is isolated in 68% yield, based on di-tert-butyl succinate.

m.p.: 123°–124° C.; UV (MeOH, $\lambda_{max}$, $\epsilon$): 222 (10200) 288 (12900).

$C_{19}H_{26}NO_4Cl$ calc.: C 62.03; H 7.12; N 3.81; Cl 9.64; found: C 62.08; H 7.15; N 3.75; Cl 9.70.

EXAMPLE 3

60 ml of methanol and 30 ml of 30% sodium methylate in methanol are added to 5.03 g of the compound of formula (6) obtained according to Example 1 (or of the corresponding Z isomer) and, under a nitrogen atmosphere, the mixture is heated for 40 minutes to 60° C.

The reaction mixture is poured into ethyl acetate and neutralised with 1N hydrochloric acid and washed with a concentrated solution of sodium chloride. The organic phase is dried over sodium sulfate and concentrated by rotary evaporation. Chromatography over silica gel (elution with a 4:1 mixture of toluene and ethyl acetate affords 2.34 g (60% of theory) of the crystalline compound of formula (8)

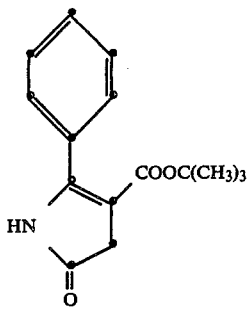
(8)

with a melting point of 153°–154° C.

$C_{15}H_{17}NO_3$ calc.: C 69.48; H 6.61; N 5.40; found: C 69.22; H 6.61; N 5.32.

EXAMPLE 4

100 g of diethyl benzoylsuccinate and 111 g of ammonium acetate are boiled under reflux in 300 ml of glacial acetic acid for 16 hours. The reaction mixture is poured into 3 liters of cold water. A crystalline precipitate is formed which is isolated by suction filtration and washed with 500 ml of water. The crude product is recrystallised in methylene chloride, affording 48.9 g of crystals of formula (9)

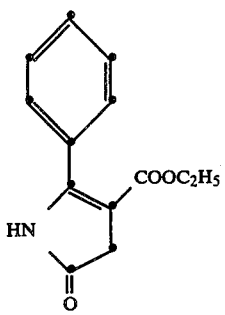
(9)

m.p.: 174° C.

$C_{13}H_{13}NO_3$ calc.: C 67.52; H 5.67; N 6.06; found: C 67.00; H 5.71; N 5.97.

EXAMPLE 5

1.55 g of sodium and 0.02 g of the sodium salt of bis-2-ethylhexyl sulfosuccinate (emulsifier) are stirred at reflux temperature in 27 ml of tert-amyl alcohol until the reaction is complete. To the clear solution are added, at 100° C., 6 g of 4-chlorobenzonitrile followed by the addition over 30 minutes of 5.1 g of the pyrrolinone of formula (9), obtained according to Example 4, in portions.

The reaction mixture is stirred at 100° C. for one hour and then poured into 200 ml of cold water. The mixture is stirred for one hour at reflux temperature and steam is subsequently introduced for one hour in order to remove the organic solvent. The pigment suspension is filtered and the filter cake is dried in vacuo at 80° C., affording 7.2 g (74%) of the pigment of formula (10)

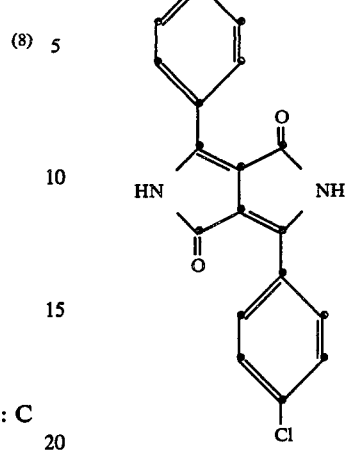
(10)

which colours PVC red.

Absorption in the visible range/in NMP, $\lambda_{max}$ $\epsilon$): 471 (25300), 510 (34100)

$C_{18}H_{11}N_2O_2Cl$: calc.: C 66.98; H 3.44; N 8.68; found: C 66.92; H 3.60; N 8.54.

EXAMPLE 6

The procedure of Example 1 is repeated, using diisopropyl succinate instead of di-tert-butyl succinate.

The oily crude product obtained after extraction is heated in 1.5% sodium methoxide in methanol for 30 minutes at 60° C. The reaction mixture is subsequently allowed to cool to room temperature and then taken up in ethyl acetate, neutralised with 1N hydrochloric acid and washed with a concentrated solution of sodium chloride until neutral. After drying over sodium sulfate, filtration and concentration, the product of the formula

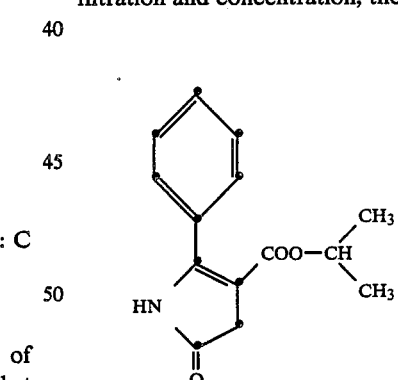

is isolated in a yield of 39%, based on diisopropyl succinate. A sample, recrystallised from a mixture of methylene chloride and hexane, melts at 148°–150° C.

$C_{14}H_{15}NO_3$ calc.: C 68.56; H 6.16; N 5.71; found: C 68.45; H 6.25; N 5.75

EXAMPLE 7

The procedure of Example 1 is repeated, using terephthalonitrile instead of benzonitrile.

After chromatography over silica gel (elution with a 4:1 mixture of toluene and ethyl acetate), 1.81 g (5% of theory, based on the di-tert-butyl succinate) of the compound of the formula

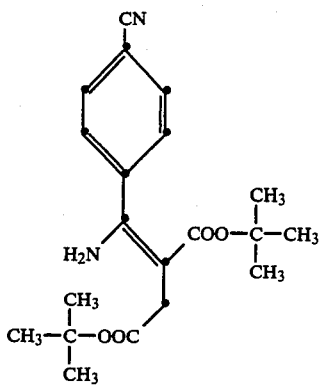

(or of the corresponding Z isomer) are isolated in the form of colourless crystals.

m.p. 158°–159° C.; UV (MeOH $\lambda_{max}$, $\epsilon$) 230 (16500), 265 (11400), 305 (sh).

$C_{20}H_{26}N_2O_4$ calc.: C 67.02; H 7.31; N 7.82; found: C 67.03; H 7.39; N 7.74.

EXAMPLE 8

The procedure of Example 1 is repeated, using isophthalonitrile instead of benzonitrile. The product of the formula

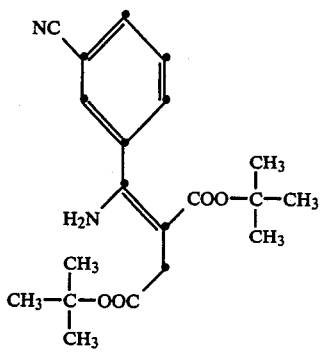

(or the corresponding Z isomer) can be isolated in a yield of 62.3%.

m.p. 112°–114° C.; UV (MeOH $\lambda_{max}$, $\epsilon$) 225 (14200), 275 (sh), 288 (9600).

$C_{20}H_{26}N_2O_4$ calc.: C 67.02; H 7.31; N 7.82; found: C 67.43; H 7.25; N 8.56.

EXAMPLE 9

1.0 g of the compound of the formula

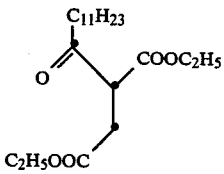

and 2 g of ammonium acetate are boiled in 5 ml of glacial acetic acid for 16 hours at 100° C. The mixture is poured into water and extracted with ethyl acetate. The organic phase is washed with a concentrated solution of sodium chloride, dried over sodium sulfate and filtered, and the filtrate is concentrated. After recrystallisation from hexane, 490 g (56% of theory) of crystalline product of the formula

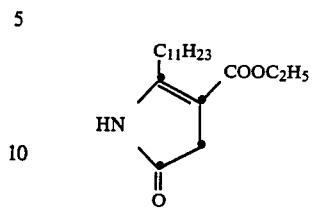

are obtained.

m.p. 61°–62° C.

$C_{18}H_{31}NO_3$ calc.: C 69.86; H 10.10; H 4.53; found: C 69.83; H 10.15; N 4.55.

EXAMPLE 10

The procedure of Example 1 is repeated, using a nitrile of the formula

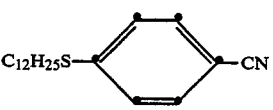

instead of benzonitrile. After chromatography over silica gel (elution with methylene chloride), the product of the formula

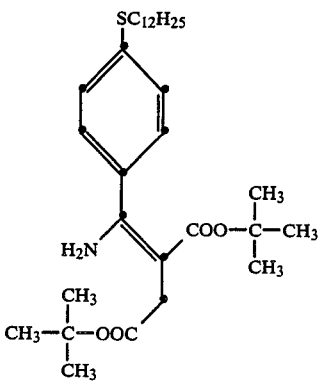

(or the corresponding Z isomer) is isolated in 29% yield as a yellow oil. Crystallisation from hexane affords a colourless product with a melting point of 41°–42° C.

$C_{31}H_{51}NO_4S$ calc.: C 69.75; H 9.63; N 2.62; found: C 69.72; H 9.61; N 2.52.

EXAMPLE 11

The procedure of Example 1 is repeated, using 4-cyanopyridine instead of benzonitrile. The compound of the formula

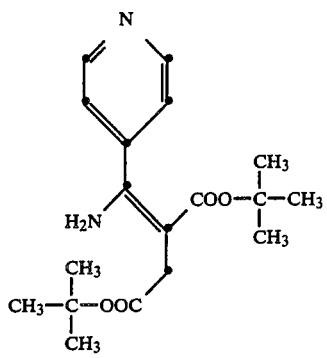

(or the corresponding Z isomer) is isolated in 40% yield.

m.p. 187°–188° C.

$C_{18}H_{26}N_2O_4$ calc.: C 64.65; H 7.84; N 8.38; found: C 64.52; H 7.86; N 8.30.

EXAMPLE 12

22.7 g of the compound of the formula

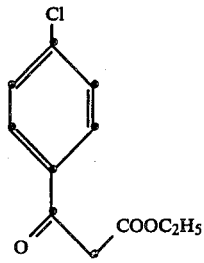

13,4 g of chloroacetic ester and 15.2 g of potassium carbonate powder are boiled under reflux in 60 ml of acetone and 40 ml of dimethoxyethane for 22 hours. The reaction mixture is allowed to cool to room temperature and then filtered, and the filtrate is washed with hexane. The filtrate is then concentrated by rotary evaporation and the compound of the formula

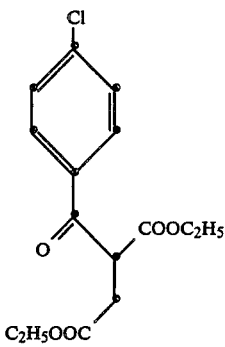

is isolated in practically quantitative yield. This compound may be directly used further as a crude product. The crude product and 78.7 g of ammonium acetate are boiled under reflux in 90 ml of glacial acetic acid for 2½ hours. The mixture is poured into ice/water and the precipitated crude product is isolated by filtration. Recrystallisation in a mixture of ethanol and water affords 16 g (60% of theory) of the crystalline product of the formula

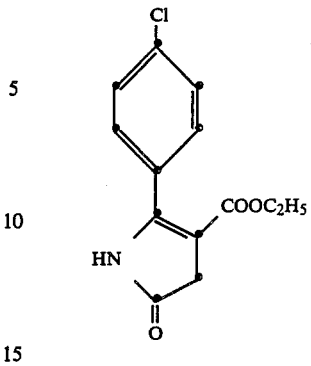

m.p. 195°–196° C.

$C_{13}H_{12}NO_3Cl$ calc.: C 58.77; H 4.55; N 5.27; Cl 13.34; found: C 58.77; H 4.52; N 5.20; Cl 13.37.

What is claimed is:

1. A pyrrolinone of the formula

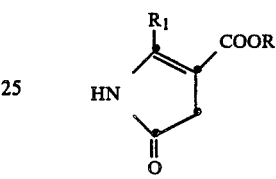

wherein $R_1$ is a radical of the formula

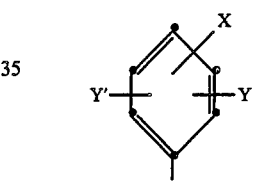

wherein each of X, Y and Y' independently is a hydrogen or halogen atom, a carbamoyl, trifluoromethyl, cyano, $C_2$–$C_6$-alkylcarbamoyl, $C_1$–$C_6$-alkyl, $C_1$–$C_6$-alkoxy, $C_1$–$C_6$-alkylmercapto, $C_2$–$C_6$-alkoxycarbonyl, $C_2$–$C_6$-alkanoylamino or $C_2$–$C_6$-dialkylamino group; or is a phenoxy, phenylmercapto, phenoxycarbonyl, phenylcarbamoyl or benzoylamino group each unsubstituted or substituted by halogen, $C_1$–$C_6$-alkyl or $C_1$–$C_6$-alkoxy, at least one of the substituents X, Y and Y' being a hydrogen atom, and R is $C_1$–$C_{18}$-alkyl, cyclohexyl, phenyl or said phenyl substituted by nitro, chlorine, $C_1$–$C_6$-alkyl or $C_1$–$C_6$-alkoxy.

2. A pyrrolinone according to claim 1, wherein $R_1$ is a radical of the formula

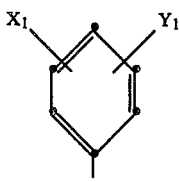

wherein one of the substituents $X_1$ and $Y_1$ is a hydrogen, chlorine or bromine atom, a methyl, cyano, N,N-dimethylamino, N,N,diethylamino, $C_1$–$C_6$alkoxy, $C_2$–$C_4$- alkoxycarbonyl or $C_2$-$C_4$alkylcarbamoyl group, or a phenylcarbamoyl group which is unsubstituted or substituted by chlorine, methyl or methoxy, and the other substitutent is a hydrogen atom, and R is $C_1$-$C_{12}$alkyl or phenyl.

3. A pyrrolinone according to claim 2, wherein R is a $C_1$-$C_4$alkyl group.

* * * * *